(12) United States Patent
Jedema

(10) Patent No.: US 8,936,947 B2
(45) Date of Patent: Jan. 20, 2015

(54) SENSOR MEASURING METHOD AND SENSING APPARATUS

(75) Inventor: Friso Jacobus Jedema, Eindhoven (NL)

(73) Assignee: NXP, B.V., Eindhoven (NL)

( * ) Notice: Subject to any disclaimer, the term of this patent is extended or adjusted under 35 U.S.C. 154(b) by 874 days.

(21) Appl. No.: 13/030,466

(22) Filed: Feb. 18, 2011

(65) Prior Publication Data

US 2011/0256634 A1 Oct. 20, 2011

(30) Foreign Application Priority Data

Feb. 19, 2010 (EP) ..................................... 10154152

(51) Int. Cl.
*G01N 33/553* (2006.01)
*G01N 33/543* (2006.01)
(52) U.S. Cl.
CPC ......... *G01N 33/5438* (2013.01); *Y10S 436/806* (2013.01)
USPC ............................ 436/526; 436/525; 436/806
(58) Field of Classification Search
None
See application file for complete search history.

(56) References Cited

U.S. PATENT DOCUMENTS

| 2010/0052080 A1 | 3/2010 | Garcia Tello et al. |
| 2012/0119727 A1 | 5/2012 | Prins et al. |

FOREIGN PATENT DOCUMENTS

| WO | 2006/079998 A1 | 8/2006 |
| WO | 2006/134546 A2 | 12/2006 |
| WO | 2007/060601 A1 | 5/2007 |
| WO | 2008/132656 A2 | 11/2008 |
| WO | 2009/024922 A2 | 2/2009 |
| WO | 2009/037636 A1 | 3/2009 |
| WO | 2009/047703 A1 | 4/2009 |
| WO | 2010/044007 A2 | 4/2010 |

OTHER PUBLICATIONS

Janssen, X.J.A. et al. "On-Chip Manipulation and Detection of Magnetic Particles for Functional Biosensors," Biosensors and Bioelectronics 23, pp. 833-838 (2008).
Extended European Search Report for European Patent Application No. 10154152.2 (Jul. 2, 2010).

*Primary Examiner* — Chris L Chin

(57) ABSTRACT

A method of performing a measurement with a sensor having a sensing surface and at least one capture molecule attached to the sensing surface for forming a binding pair with an analyte of interest, the binding pair having a flexible spatial orientation, the method comprising capturing the analyte of interest with the capture molecule, thereby forming the binding pair in an initial spatial orientation; applying a first electromagnetic force to the sensing surface to alter the spatial orientation of the binding pair; and performing a sensor measurement with the binding pair in the altered spatial orientation. A sensor apparatus implementing this method is also disclosed.

17 Claims, 4 Drawing Sheets

SENSOR MEASURING METHOD AND SENSING APPARATUS

Figure 1:
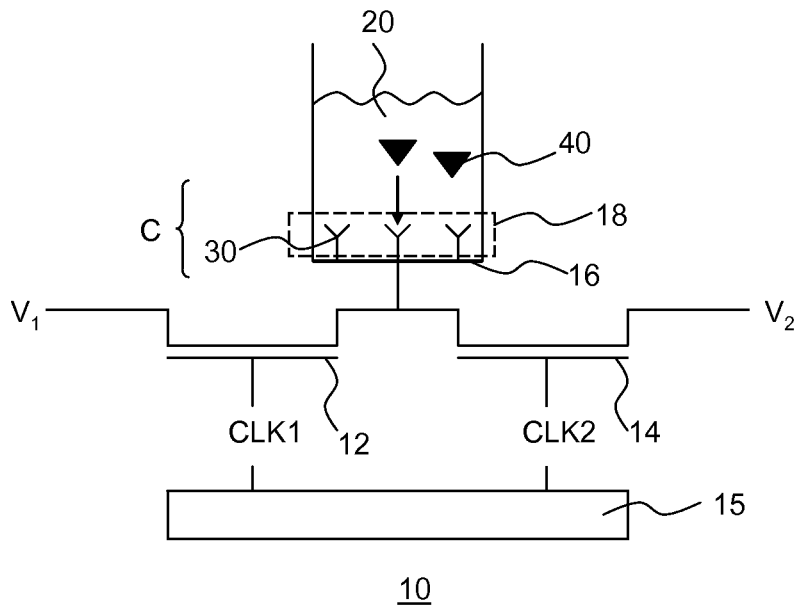

This application claims the priority under 35 U.S.C. §119 of European patent application no. 10154152.2, filed on Feb. 19, 2010, the contents of which are incorporated by reference herein.

FIELD OF THE INVENTION

The present invention relates to a method of performing a measurement with a sensor having a sensing surface and at least one capture molecule attached to the sensing surface for forming a binding pair with an analyte of interest.

The present invention further relates to a sensing apparatus comprising a sensor having a sensing surface and at least one capture molecule attached to the sensing surface for forming a binding pair with an analyte of interest.

BACKGROUND OF THE INVENTION

A biosensor may be denoted as a device which may be used for the detection of an analyte that combines a biological component with a physicochemical or physical detector component.

For instance, a biosensor may be based on the phenomenon that capture molecules immobilized on a surface of a biosensor may selectively hybridize with target molecules in a fluidic sample, for instance when an antibody-binding fragment of an antibody or the sequence of a DNA single strand as a capture molecule fits to a corresponding sequence or structure of a target molecule. When such hybridization or sensor events occur at the sensor surface, this may change the electrical properties of the surface and the volume directly above the surface which can be detected as the sensor event.

Many suitable specific binding pair candidates are known per se, which are typically based on a lock-and-key type interaction between a receptor molecule and a molecule, e.g. a drug. This makes a sensing apparatus such as an assay-based apparatus particularly suitable to determine the presence or absence of specific proteins and other biological compounds such as DNA, RNA, hormones, metabolites, drugs and so on, or to determine the activity and function of active and catalytic biomolecules such as proteins, peptides, prions, enzymes, aptamers, ribozymes and deoxyribozymes. For instance, immunoassays are already used to determine the specific amount of specific proteins in body fluids to aid further diagnosis and treatment.

Due to advances in semiconductor technology, it has become feasible to detect single capture events on a sensing surface of such sensors. An example of such a sensor is disclosed in PCT patent application WO 2009/047703, in which a capture molecule forms an insulating layer of a capacitor, with the plates of the capacitor formed by a conductive sensing surface and a fluid sample respectively. A capture event causes a change in the dielectric constant of the insulating layer including the volume directly above the sensor surface in which a capture event takes place, which affects the capacity of the capacitor. The change in capacitance can be measured, e.g. as a bias on a current through a transistor, as is the case in this application.

An alternative arrangement is disclosed in PCT patent application WO 2008/132656, in which an extended gate field effect transistor is disclosed with capture molecules on the surface of the extended gate, such that the gate potential of the transistor can be altered by capture events.

Another type of biosensor that has been gaining considerable attention is an assay-type biosensor in which antibodies are bound to magnetic beads, which are attracted to a sensing surface carrying further antibodies by a magnetic force, with the analyte of interest binding the magnetic beads to the sensing surface by forming a binding pair with the antibodies and the further antibodies. Examples of such assays are for instance given in PCT patent application WO 2007/060601.

A problem associated with such type of sensors is that contamination of the sensing surface with non-specific binding events also affects a sensing event, i.e. introduces noise to the measurement, thus decreasing the reliability of the sensor reading. This is detrimental to any type of sensor that has a sensing surface adapted to measure the formation of specific binding pairs, and in particular to the type of sensor such as disclosed in WO 2009/047703, because for such sensors a single non-specific binding event is likely to introduce noise at a magnitude comparable to the magnitude of the signal generated by the binding pair.

SUMMARY OF THE INVENTION

The present invention seeks to provide a method of performing a measurement with a sensor having a sensing surface and at least one capture molecule attached to the sensing surface for forming a binding pair with an analyte of interest that is less susceptible to noise.

The present invention further seeks to provide a sensing apparatus that implements the inventive method.

According to a first aspect of the present invention, there is provided a method of performing a measurement with a sensor having a sensing surface and at least one capture molecule attached to the sensing surface for forming a binding pair with an analyte of interest, the binding pair having a flexible spatial orientation, the method comprising capturing the analyte of interest with the capture molecule, thereby forming the binding pair in an initial spatial orientation applying a first electromagnetic force to the sensing surface to alter the spatial orientation of the binding pair; and performing a sensor measurement with the binding pair in the altered spatial orientation.

The present invention is based on the realization that many binding pairs have large conformational freedom. Moreover, as binding pairs typically exhibit either a significant permanent dipole and/or some charged atoms, an electromagnetic force may be used to interact with the dipole and/or charge of the binding pair to manipulate the conformation of the binding pair. The magnitude of the electromagnetic force must be less than the binding energy of the binding pair such that the binding pair is not dissociated upon application of the electromagnetic force.

Two principal scenarios may occur. In the first scenario, a repulsive electromagnetic force is applied, such that both the contaminants and the binding pair are moved away from their initial position. This scenario is particularly applicable when the contaminant is also affected by the applied electromagnetic force. This is for instance the case in an assay-based sensor such as disclosed in WO 2007/060601, in which unbound magnetic beads may contaminate the sensing surface. The application of the repulsive force moves the contaminants such as unbound beads much further away from the sensing surface than the binding pair, as the capture molecule of the binding pair is anchored to the sensing surface. In this case, a single measurement after removal of the unbound contaminants may suffice to improve the signal-to-noise ratio of the sensor signal.

In a second scenario, the electromagnetic force does not significantly affect the adhesive bond between the contaminant and the sensing surface. In this scenario, the method may further comprise performing a sensor measurement with the binding pair in the initial spatial orientation; and deriving a sensor signal induced by the binding pair from the sensor measurement with the binding pair in the initial spatial orientation and the sensor measurement with the binding pair in the altered spatial orientation. In other words, the sensor signal is modulated by periodically altering the spatial orientation of the binding pair only, such that the constant contribution of the contaminants to the sensor signal can be filtered out.

In an embodiment, this is achieved by calculating the sensor signal induced by the binding pair from a difference between the sensor measurement with the binding pair in the initial spatial orientation and the sensor measurement with the binding pair in the altered spatial orientation. It is pointed out that this modulation does not necessarily have to be between to 2 discrete or steady states, but may also involve a continuous change if the time in between measurements is shorter than the adaptation to a new discrete spatial orientation.

Preferably, the steps of performing a sensor measurement with the binding pair in the initial spatial orientation, applying the first electromagnetic force and performing the sensor measurement with the binding pair in the altered spatial orientation are repeated at a predefined frequency In an embodiment, the method further comprises applying a further electromagnetic force to the sensing surface to bring the binding pair in the initial spatial orientation. Preferably, one of the first and further electromagnetic force is an attractive force and the other of the first and further electromagnetic force is a repulsive force. This has the advantage that a controlled modulation between the initial orientation and the altered orientation of the binding pair can be achieved.

The electromagnetic force used in the present invention may be an electric force or a magnetic force.

In accordance with a further aspect of the present invention, there is provided a sensing apparatus comprising a sensor having a sensing surface and at least one capture molecule attached to the sensing surface for forming a binding pair with an analyte of interest, the binding pair having a flexible spatial orientation, the sensing apparatus further comprising means for applying a first electromagnetic force to the sensing surface to alter the spatial orientation of the binding pair, wherein the sensing apparatus is adapted to perform a sensor measurement with the binding pair in the altered spatial orientation. In an embodiment, the electromagnetic force may be applied by the sensor electrode.

The sensing apparatus of the present invention benefits from an improved signal-to-noise ratio, as previously explained.

The sensing apparatus further may be adapted to perform a sensor measurement with the binding pair in the initial spatial orientation, wherein the sensing apparatus further comprises processing means for deriving a sensor signal induced by the binding pair from the sensor measurement with the binding pair in the initial spatial orientation and the sensor measurement with the binding pair in the altered spatial orientation, such as the calculation of a difference between the sensor measurement with the binding pair in the initial spatial orientation and the sensor measurement with the binding pair in the altered spatial orientation such that the contribution of the contaminant to the sensor signal is filtered out.

Preferably, the sensing apparatus further comprises a controller for repeatedly performing a sensor measurement with the binding pair in the initial spatial orientation, applying the first electromagnetic force and performing the sensor measurement with the binding pair in the altered spatial orientation at a predefined frequency such that the signal-to-noise ratio of the sensor signal may be further improved by modulation of the sensor signal with the periodic displacement of the binding pair. To this end, the sensing apparatus may comprise means for applying a first electromagnetic force are adapted to alternate between an attractive electromagnetic force and a repulsive electromagnetic force for an improved control over this modulation.

BRIEF DESCRIPTION OF THE EMBODIMENTS

Figure 2:
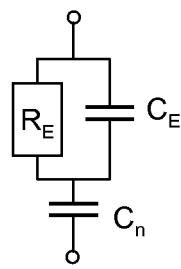
Figure 3:
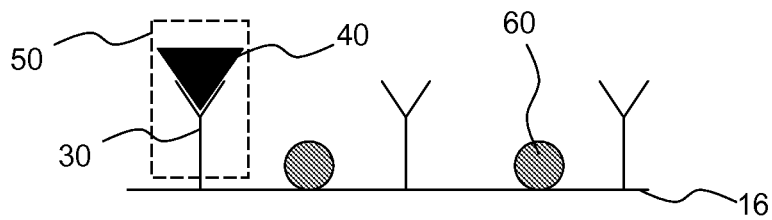
Figure 4:
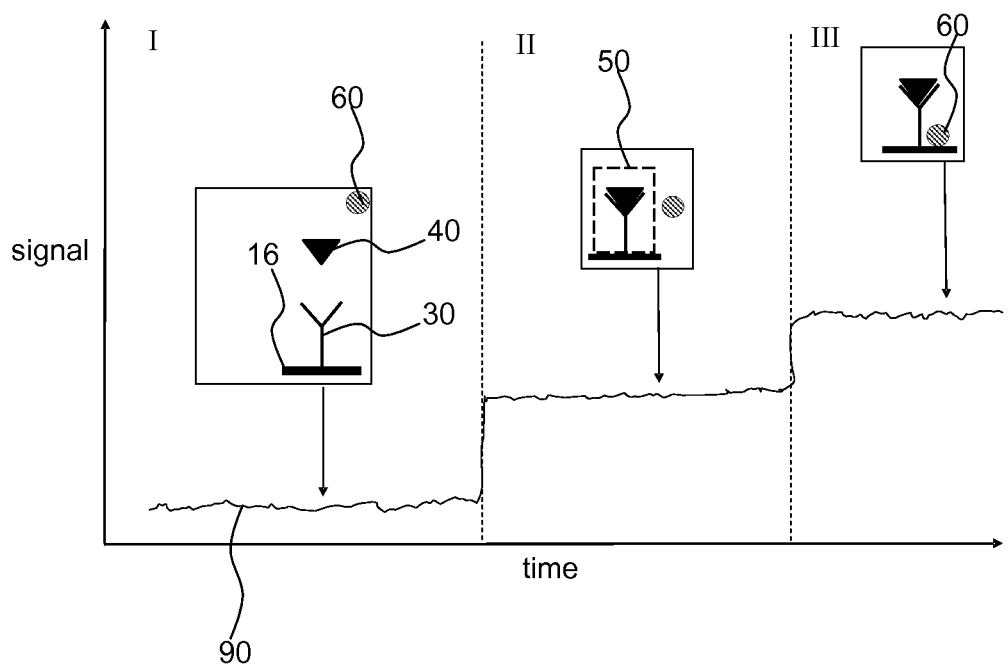
Figure 5:
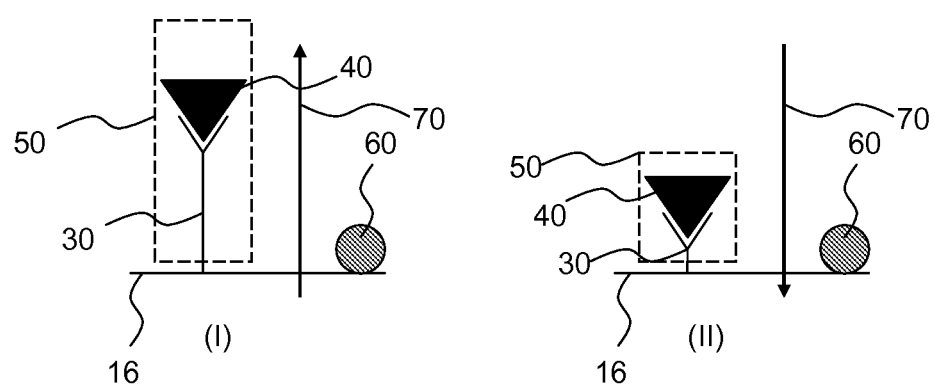
Figure 6:
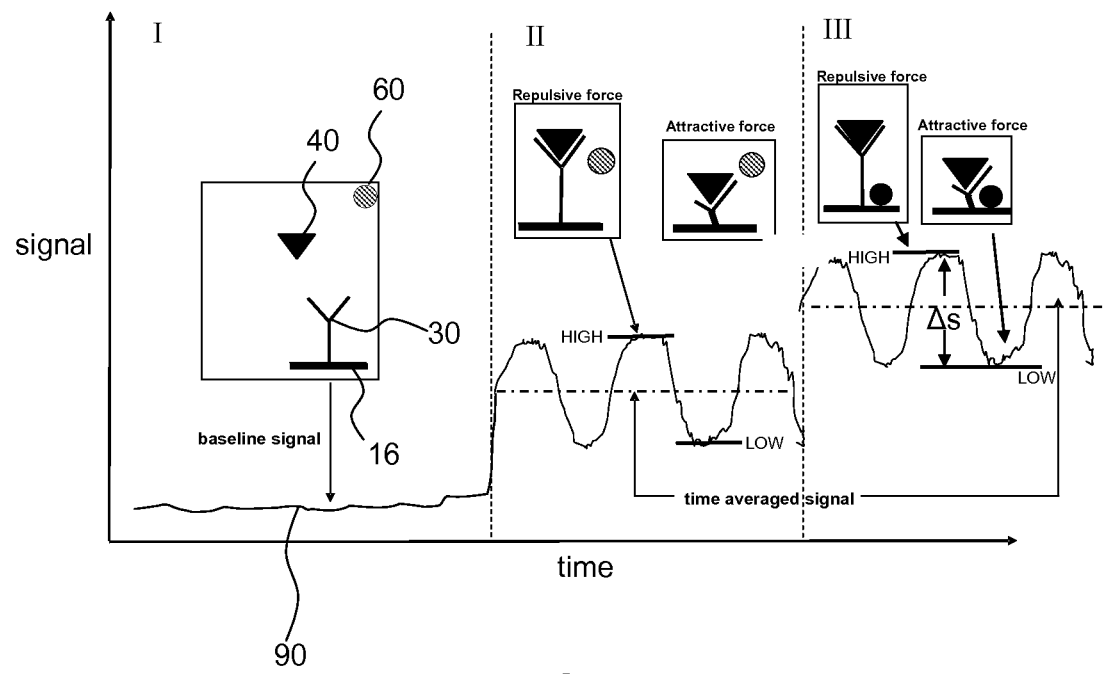
Figure 7:
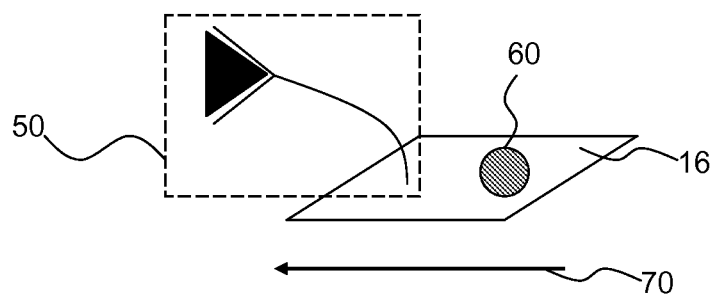
Figure 8:
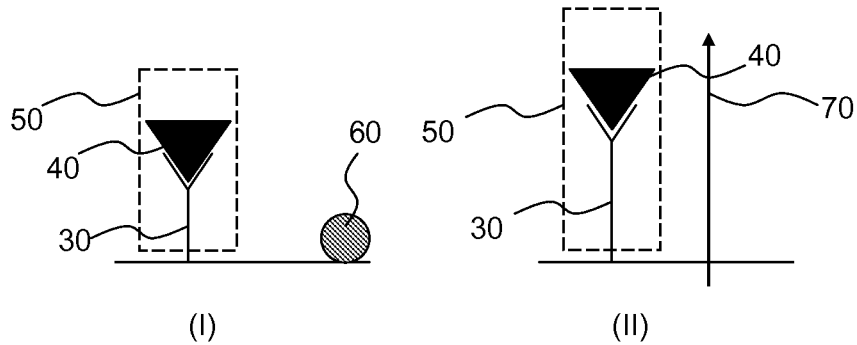
Figure 9:
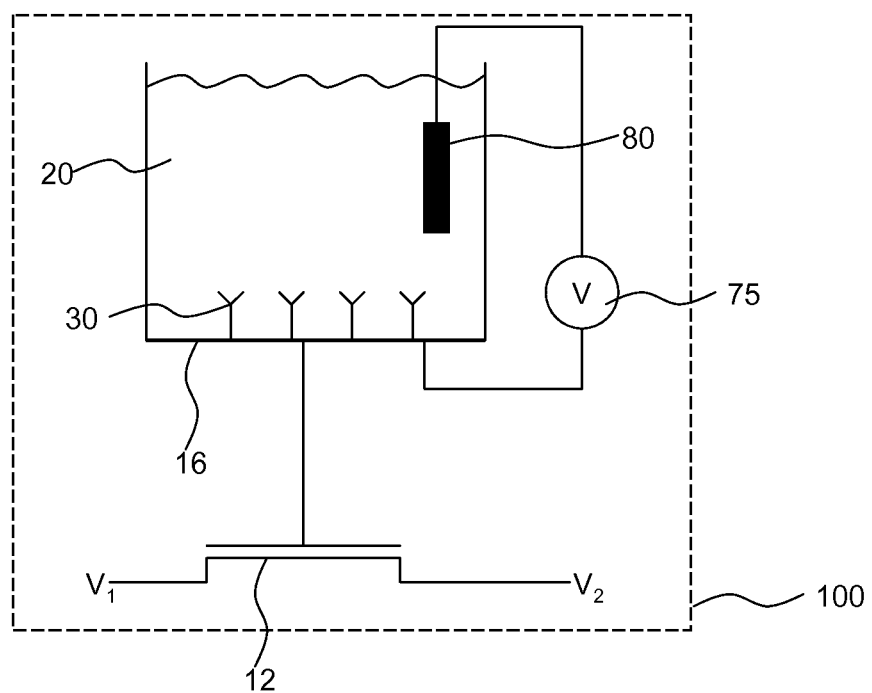

Embodiments of the invention are described in more detail and by way of non-limiting examples with reference to the accompanying drawings, wherein FIG. 1 schematically depicts a prior art sensor device;

FIG. 2 schematically depicts an electrical replacement model of the prior art sensor device;

FIG. 3 schematically depicts a problem associated with certain types of sensor devices;

FIG. 4 schematically depicts the effect of contamination of the sensing surface on the sensor signal of the certain types of sensor devices;

FIG. 5 schematically depicts a first embodiment of the method of the present invention;

FIG. 6 schematically depicts the effect of the method of the present invention on a sensor signal;

FIG. 7 schematically depicts another embodiment of the method of the present invention;

FIG. 8 schematically depicts yet another embodiment of the method of the present invention; and FIG. 9 schematically depicts a non-limiting example of a sensor apparatus of the present invention.

DETAILED DESCRIPTION OF EMBODIMENTS

It should be understood that the Figures are merely schematic and are not drawn to scale. It should also be understood that the same reference numerals are used throughout the Figures to indicate the same or similar parts.

The present invention is applicable to all types of sensors in which a sensor output signal is influenced by the formation of a binding pair on a sensor surface, independent of the nature of the sensor output signal, e.g. derived from a voltage, a charge, a capacitance, a current, an optical signal, a magnetic signal and so on.

The present invention is further applicable to all types of sensors that have a sensing surface that is functionalized with a capture molecule for forming a binding pair with an analyte of interest. The sensing surface may be functionalized with the capture molecule in any suitable form, such as through covalent or ionic bonding, self-assembly of the capture molecule on the sensing surface, adhesion, hydrogen bonding or any other suitable type of chemical bonding.

The analyte of interest may be any molecule of which concentration or presence as such is to be determined. Examples of analytes of interest are molecular targets such as DNA, RNA, metabolites, viruses, proteins, enzymes, hormones, peptides, nucleic acids and cellular targets such as pathogen cells, bacterial cells and fungal cells. The analyte of interest may exist as such in a sample that is analyzed or may be formed in situ in a sensor device e.g. via a reaction that takes place in the device. If the sensor is used to monitor a reaction, the analyte of interest may for example be the starting product of the reaction or a reaction product.

The capture molecule may be any suitable capture molecule, such as a receptor, an antibody, a complementary DNA or RNA sequence, a synthetic receptor such as a molecularly imprinted polymer and so on, as long as the capture molecule is capable of specifically binding to the analyte of interest.

In the context of the present, a binding pair is a combination of two moieties (molecules) A and B with specific binding between the two moieties wherein moiety A binds to moiety B more strongly or preferentially than to other molecules and shows little or no cross reactivity with other molecules. In general the affinity constant (Ka) for specific binding between moiety A and B is at least $10^6$ l/mol.

FIG. 1 depicts an embodiment of the sensor device 10 of WO 2009/047703. The sensor device 10 comprises a first transistor 12 and a second transistor 14 coupled in series between a first voltage source $V_1$ and a second voltage source $V_2$ such as the supply voltage and ground respectively. The first transistor 12 and the second transistor 14 are controlled by respective control signals CLK1 and CLK2 from a control circuit 15, e.g. a clock signal generator.

A node in the source/drain connection between the first transistor 12 and a second transistor 14 is connected to an electrode 16 carrying a number of capture molecules 30 for capturing an analyte of interest 40 from a sample 20. The electrode 16 and the sample 20 form the capacitor plates of a capacitor C, which are separated by a dielectric layer 18 formed by the one or more capture molecules 30.

In operation, the capacitor C is charged by connecting the electrode 16 to voltage source $V_1$ through the first transistor 12. The subsequent occurrence of a capture event, i.e. the formation of a binding pair between a capture molecule 30 and a molecule of the analyte of interest 40 induces a change in the dielectric constant of the dielectric layer 18, thus affecting the capacitance of the capacitor C. Hence, upon read-out of the capacitor C by switching the first transistor to a non-conductive state whilst switching the second transistor 14 to a conductive state, the change in capacitance can be derived from the charge flowing from the electrode 16 to the second voltage source $V_2$.

The changes in the dielectric constant of the dielectric layer 18 are typically affected by changes in the surface potential as well as a volumetric contribution to the dielectric constant, as will be explained in more detail with the aid of FIG. 2.

To elaborate some more: the signal (S) of the sensor 10 is a function of 3 impedances, as shown in FIG. 2. Each impedance is sensitive to an approaching analyte particle, i.e as shown in equation (1):

$$S = S(C_n, R_E, C_E) \quad (1)$$

The electrode capacitance $C_n$, the electrolyte resistance $R_E$ and the electrolyte capacitance $C_E$ are all determined by the geometrical size of the sensor electrode. In the absence of an analyte particle, these impedances may be expressed as shown in equations (2)-(4):

$$C_n = c_0 \pi \left(\frac{d}{2}\right)^2 \quad (2)$$

$$R_E = \frac{16}{3\pi^3 d} \frac{1}{\sigma_E} \quad (3)$$

$$C_E = \frac{3\pi^2 d}{16} \varepsilon_0 \varepsilon_E \quad (4)$$

Here, d is the diameter of the electrode, c0 is the capacitance density of the dielectric layer 18, e.g. a thiolated SAM or thiolated DNA hybidization probes, $\sigma E$ is the dc resistivity of the electrolyte, $\in$o is the permittivity in vacuum (8.854× 10-12 C/V-m) and $\in$E is the relative permittivity of the electrolyte solution. Typical numbers would be d=130 nm for PT2, c0=0.01 F/m2 for a thiolated SAM, $\sigma$E=1.57 S and $\in$E=75.4 for a 150 mM Phosphate Buffered Solution comprising 2 g NaCl, 0.2 g KCl, 0.2 g Na2HPO4 and 0.2 g KH2PO4 in 1 liter deionized water.

yielding typical numbers for $C_n$=133 aF, $C_{E,0}$=160 aF and $R_{E,0}$=2.6 MΩ for the nano electrode in physiological solutions. Note that the impedances of equations (2)-(4) can be considered as the fundamental impedances relevant for the (bio)sensor 10. These impedances are affected in the presence of an analyte particle or biomolecules in the (near) proximity of the electrode surface.

The accuracy of such a read-out can be negatively affected by non-specific binding events affecting the dielectric constant of the capacitor C. This is shown in FIG. 3, in which a specific binding between the capture molecule 30 and the analyte of interest 40 has been formed in the form of binding pair 50, whereas a non-specific binding between a contaminant 60 and the sensing surface 16 has also occurred. The contaminant 60 may be any contaminant, including the analyte of interest 40 engaging in a non-specific binding with the sensing surface 16.

As both the formation of the binding pair 50 and the non-specific binding of the contaminant 60 to the sensing surface 16 affect the dielectric constant of the dielectric layer 18, the sensor output signal also becomes 'contaminated', as this signal is correlated to the dielectric constant. In other words, the presence of the contaminant 60 in the dielectric layer 18 introduces noise to the sensor output signal. This is particularly detrimental if the contaminant 60 binds to the sensing surface 16 for a prolonged period of time, i.e. for several measurement cycles, as the noise will become a constant contribution to the sensor output signal, such that it cannot be averaged out using conventional noise filtering techniques.

The effect of the contribution of the contaminant 60 on the sensor output signal is schematically depicted in FIG. 4. In region I, the dielectric layer 18 over the sensing surface 16 comprises a contribution from the capture molecule 30 only, resulting in a baseline sensor output signal 90. Upon formation of the binding pair 50 in region II, the sensor output signal 90 ramps up to an increased level (or ramps down to a decreased level; not shown), with a further increase (or decrease) caused by the non-specific binding of the contaminant 60 to the sensing surface 16 in region III.

Hence, at the point where the sensor output signal 90 contains a contribution from the binding pair 50 as well as from the contaminant 60, it is not at all straightforward to extract the binding pair 50 contribution from the sensor output signal 90. Another problem occurs when the sensor output signal 90 contains a contribution from the contaminant 60 only, in which case the sensor output signal 90 may lead to the determination of a false positive, i.e. the incorrect determination of the formation of a binding pair 50.

It is pointed out that FIG. 4 is not a realistic reflection of the time-dependent nature of the sensor signal 90 as it will be apparent that specific and non-specific binding events typically occur with at least some temporal overlap, e.g. simultaneously. Also, although only positive steps are shown, it should be understood that such steps, i.e. such contributions to the overall sensor signal may be positive as well as negative. The discrete steps in the sensor output signal 90 are artificial and introduced for the purpose of demonstrating the various contributions to the overall sensor output signal 90 only.

It is noted that although the above problem description has been based on the sensor of FIG. 1, the problem equally exists in other types of sensors relying on measuring change in a sensor output signal upon the occurrence of the formation of a binding pair on a sensing surface 16, e.g. extended gate field effect transistors (FETs), FETs having chemically modified gate electrodes exposed to a sample, sensor devices adapted to derive an optical or magnetic signal from magnetic beads bound to a sensing surface via a binding pair and so on.

The present invention has been based on the realization that most binding pairs 50 consist of at least one relatively large molecule, e.g. a sequence of nucleotides, such that the binding pair 50 has significant conformational freedom, i.e. can be reoriented, and have either a large permanent dipole moment or one or more charges in at least one of the analyte of interest 40 and the capture molecule 30, which can be used as a handle to induce a change between different orientations and/or conformations of the binding pair 50 by subjecting the sensing surface 16, which includes the binding pair 50 when formed to an electromagnetic force such as an electric field or a magnetic field.

In other words, when considering FIG. 2 and its detailed description, the present inventor has realized that the sensitive volume above the electrode surface is not homogeneous, and/or the current injection density across the dielectric layer 18 may not be homogeneous, such that a change in signal can be observed by changing the spatial orientation of the binding pair.

The principle of the method of the present invention is depicted in FIG. 5. As shown on the left hand side, the application of a repulsive electromagnetic force 70 repels the binding pair 50 from the sensing surface 16. For instance, the repulsive electromagnetic force 70 may cause the binding pair 50 to stretch in the direction of this force. At the same time, contaminant 60, which does not comprise a charge or a large permanent dipole, (or is more strongly bound to the surface than the applied force, is not affected by the application of the repulsive electromagnetic force 70. In other words, the non-specific binding between the contaminant 60 and the sensing surface 16 is not affected. A first sensor output signal 90 may be generated in a first measurement with the binding pair 50 in position (I) as shown in the left-hand panel of FIG. 5.

Subsequently, an attractive electromagnetic force 70 may be applied to the sensing surface 16 as shown in the right-hand panel of FIG. 5, after which a second sensor output signal 90 may be generated in a second measurement. The application of attractive electromagnetic force 70 forces the binding pair 50 into an orientation, i.e. conformation, in which the binding pair 50 has adopted a more compact shape. This is due to the fact that the permanent dipole moment is realigned or charge(s) of the binding pair 50 is (are) attracted to the sensing surface 16 by the attractive electromagnetic force 70. A second sensor output signal 90 may be generated with the binding pair 50 in position (II) as shown in the left-hand panel of FIG. 5.

It should be appreciated that the electromagnetic force 70 applied to the binding pair 50 should not exceed the strength of the bond between the capture molecule 30 and the analyte of interest 40. In other words, it has to be ensured that the applied electromagnetic force 70 does not disassociate the analyte of interest 40 from the capture molecule 30.

The difference in orientation of the binding pair 50 in position (I) and position (II) affects the overall properties on the functionalization layer over the sensing surface 16. For instance, in case of the sensor device 10 shown in FIG. 1, the different orientations of the binding pair 50 will affect the dielectric constant of the dielectric layer 18. Similarly, if the functionalization layer is applied to a gate electrode, the changes in the orientation of the binding pair 50 as induced by the application of the electromagnetic force 70 will affect the gate potential of the gate electrode. If the analyte of interest 40 comprises a light emitting moiety such as a fluorescent probe, the changes in orientation as induced by the electromagnetic force 70 may cause a difference in the intensity of the fluorescence captured by the sensor device. From these examples, it will be appreciated that the induced orientation changes of the binding pair 50 using an electromagnetic force may be applied to a wide variety of sensor devices, such that the present invention is not limited to the sensor device 10 shown in FIG. 1.

By way of non-limiting example, the effect of the electromagnetic force induced orientation changes of the binding pair 50 on the sensor output signal 90 of the sensor device 10 as shown in FIG. 3 is shown in FIG. 6. In the first phase, in which no binding pair 50 has been formed and in which the sensing surface 16 has not been contaminated with contaminant 60, the baseline of sensor output signal 90 is unaffected by the application of a directionally alternating electromagnetic force 70.

The effect of the application of a directionally alternating electromagnetic force 70 following the formation of the binding pair 50 is clearly shown in phase II. The different orientations of the binding pair 50 induced by the application of the alternating electromagnetic force 70 causes a modulation of the sensor output signal 90 due to the fact that the value of the dielectric constant of the dielectric layer 18 in capacitor C is altered by a change in the orientation of the binding pair 50. The difference between the maximum and minimum intensity of the sensor output signal 90 is $\Delta S$.

The contribution of the contaminant 60 binding non-specifically to the sensing surface 16 is depicted in phase III of FIG. 6. Again, because the orientation of contaminant 60 is not significantly affected by the application of the alternating electromagnetic force 70, the contribution of the contaminant to the sensor output signal 90 is a steady-state, i.e. unmodulated, contribution. In the case of the sensor device 10 of FIG. 1, the sensor output signal 90 is a voltage, with the contribution to this signal from the binding pair 50 being an alternating voltage and the contribution to this signal from the contaminant 60 being a direct voltage. Consequently, the contribution to the sensor output signal 90 from the contaminant 60 can be readily filtered out using standard modulation techniques such as ac lock-in techniques.

It is noted that the modulation frequency of the sensor output signal 90 as induced by the alternating electromagnetic force 70 should not exceed the readout speed of the sensor device. For instance, in a sensor device comprising an array of 256 rows and columns of sensor elements, such readouts are typically performed at a frequency not exceeding 25 Hz for reasons explained in more detail below. In such a case, the alternating frequency of the electromagnetic force 70 should also not exceed 25 Hz. For instance, the alternating frequency of the electromagnetic force 70 may be chosen in a range from 15 to 25 Hz.

It is further noted that it may not be necessary to apply both a repulsive electromagnetic force 70 as well as an attractive electromagnetic force 70. In the absence of an electromagnetic force, the binding pair 50 will assume a minimum energy conformation, which may be altered upon application of either an attractive or repulsive electromagnetic force 70 as previously explained. If the change in conformation induced by the application of this single electromagnetic force 70 is large enough, i.e. a large enough variation $\Delta S$ is induced in the sensor output signal 90, it may suffice to apply only a single electromagnetic force 70 in a measurement cycle. In such a scenario, the binding pair 50 is modulated between its lowest energy conformation in the absence of the electromagnetic force 70 and its lowest energy conformation in the applied electromagnetic force 70, which may be attractive or repulsive.

In the embodiment shown in FIG. 5, the electromagnetic force 70 has a direction that is substantially perpendicular to the sensing surface 16 in order to induce a change in the orientation of the binding pair 50 in the same direction. However, it is equally feasible to apply the electromagnetic force 70 in a different direction, as for instance is shown in FIG. 7. Here, the electromagnetic force 70 is applied substantially in parallel to the sensing surface 16, causing a displacement of the binding pair 50 in the same direction. This embodiment is for instance particularly feasible for relatively small area sensing surfaces 16, in which the lateral displacement causes at least part of the binding pair 50 to extend beyond the area of the sensing surface 16 such that only a part of the binding pair 50 is sensed in this displaced orientation.

Alternatively, the sensing surface 16 may be used as the actuator of the electromagnetic force 70. This may be achieved in any suitable manner, e.g. by providing the sensing surface 16 with a suitably modulated signal.

It has so far been assumed that the non-specific binding of the contaminant 60 to the sensing surface 16 is not affected by the applied electromagnetic force 70. This, however, is not necessarily the case as is demonstrated in FIG. 8. For instance, in case the analyte of interest 40 acts as a linking molecule between an antibody 30 and a further antibody attached to a magnetic bead (not shown) such as for instance is the case in an ELISA assay, unbound magnetic beads may be attracted to the sensing surface 16 upon the application of an attractive electromagnetic force 70, thereby acting as a contaminant 60 on the sensing surface 16 is shown in the left-hand panel (I) of FIG. 8.

Such a contaminant 60 may be removed by the application of a repulsive electromagnetic force 70, as shown in the right-hand panel (II) of FIG. 8. Since not all thus removed contaminants 60 will return to sensing surface 16, it will be possible to filter out the contribution of contaminants 60 to the sensor output signal 90 as previously explained. The chance of contaminants 60 returning to the sensing surface 16 is even further reduced if no attractive electromagnetic force 70 is applied following the removal of the contaminants 60. In such an embodiment, the orientation of the binding pair 50 may be alternated between its lowest energy conformation in the absence of an electromagnetic force 70 and its lowest energy conformation in the presence of a repulsive electromagnetic force 70.

In another embodiment, a single sensor measurement is performed whilst applying the repulsive electromagnetic force 70 as the repulsive electromagnetic force 70 ensures that no contaminant 60 is present at the sensing surface 16. This embodiment may for instance replace a washing step to remove unbound contaminants 60, thus simplifying the use of sensor devices e.g. utilising magnetic beads.

FIG. 9 shows a non-limiting example of a sensor apparatus 100 in accordance with an embodiment of the present invention. In this embodiment, a field effect transistor 12 is conductively coupled between two voltage sources $V_1$ and $V_2$, with its gate connected to a sensing electrode 16 that has been functionalized with capture molecules 30. The sensing electrode 16 is connected to an electromagnetic force generator 75, which for instance may be a magnetic field generator or an electric field generator and so on. The electromagnetic force generator 75 may be adapted to apply an alternating electromagnetic force 70 as previously discussed.

A counter electrode 80 may also be connected to the electromagnetic force generator 75, for instance to generate an electric force between the sensing electrode 16 and the counter electrode 80. In operation, the electromagnetic force generator 75 periodically generates an electromagnetic force 70 and a sensor output signal 90 is periodically generated in accordance with any of the above discussed embodiments of the method of the present invention. It is once more reiterated that the sensor apparatus 100 may take any suitable form, such as the form of the sensor device 10 as shown in FIG. 1 and extended with an electromagnetic force generator 75 to facilitate modulation of the sensor output signal 90 as previously discussed. More generally, the sensor apparatus 100 may be any sensor apparatus that has a sensing surface 16 functionalized with one or more capture molecules 30.

The sensor apparatus 100 may further comprise signal processing circuitry (not shown) for deriving a sensor signal induced by the binding pair 50 from a first sensor measurement with the binding pair 50 in an initial spatial orientation and a further sensor measurement with the binding pair 50 in the altered spatial orientation. In other words, such signal processing circuitry is adapted to filter out contribution of the contaminants 60 from the modulated sensor output signal 90 as previously discussed. This may for instance be achieved by calculating a difference between the sensor measurement with the binding pair 50 in the initial spatial orientation and the sensor measurement with the binding pair in the altered spatial orientation 50. Other suitable approaches will be apparent to the skilled person.

The sensor apparatus 100 may further comprise a controller (not shown) for repeatedly performing a sensor measurement with the binding pair 50 in the initial spatial orientation, applying the first electromagnetic force 70 and performing the sensor measurement with the binding pair in the altered spatial orientation at a predefined frequency. For instance, for a sensor comprising an array of sensing elements of e.g. 256 rows by 256 columns, with a row-based reading of the sensor array, the predefined frequency will be related to the duration of a single readout of the whole array. For example, if a single row readout will take 150 µs (40 µs measurement time and 110 µs for sending the measured data to a signal processor), the total readout time of the array will be 256×150 µs, which is approximately 40 ms. Consequently, the modulation frequency cannot exceed 25 Hz for such a sensor. However, as the present invention may be applied to any suitable type of sensor, e.g. a sensor comprising a single row of 256 sensing elements, such a sensor would have an upper modulation frequency limit of around 1 kHz. For sensors comprising even fewer sensing elements, this frequency obviously may be further increased.

For the sake of completeness, it is further noted that the upper limit in the modulation frequency may also be determined by the time constant at which the conformation of the binding pair can be altered from its initial conformation to its further conformation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A method of performing a measurement with a sensor having a sensing surface and at least one capture molecule attached to the sensing surface for forming a binding pair with an analyte of interest, the binding pair having a flexible spatial orientation, the method comprising:
    capturing the analyte of interest with the capture molecule, thereby forming the binding pair;
    performing a sensor measurement with the binding pair in an initial spatial orientation;
    applying a first electromagnetic force to the sensing surface to alter the spatial orientation of the binding pair, wherein the magnitude of the applied first electromagnetic force is less than the binding energy of the binding pair;
    performing a sensor measurement with the binding pair in the altered spatial orientation;
    deriving a sensor signal induced by the binding pair from the sensor measurement with the binding pair in the initial spatial orientation and the sensor measurement with the binding pair in the altered spatial orientation, wherein deriving the sensor signal induced by the binding pair comprises calculating a difference between the sensor measurement with the binding pair in the initial spatial orientation and the sensor measurement with the binding pair in the altered spatial orientation; and
    repeating, at a predefined frequency, the steps of performing a sensor measurement with the binding pair in the initial spatial orientation, applying the first electromagnetic force, performing the sensor measurement with the binding pair in the altered spatial orientation, and deriving a sensor signal.

2. The method of claim 1, wherein the predefined frequency is in the interval of 15-25 Hz.

3. The method of claim 1, further comprising applying a further electromagnetic force to the sensing surface to bring the binding pair in the initial spatial orientation.

4. The method of claim 3, wherein one of the first and further electromagnetic force is an attractive force and the other of the first and further electromagnetic force is a repulsive force.

5. The method of claim 1, wherein the electromagnetic force is an electric force.

6. The method of any of claim 1, wherein the electromagnetic force is a magnetic force.

7. The method of claim 1, wherein the applied first electromagnetic force does not alter the spatial orientation of contaminants such that a signal contribution from the contaminants is filtered out from the derived sensor signal.

8. The method of claim 7, wherein the sensor signal is a voltage, with the contribution to the sensor signal from the binding pair being an alternating voltage and the contribution to the sensor signal from the contaminants being a direct voltage.

9. The method of claim 1, wherein the applied first electromagnetic force does not alter the spatial orientation of non-specifically bound elements such that a signal contribution from the non-specifically bound elements is filtered out from the derived sensor signal.

10. The method of claim 9, wherein the sensor signal is a voltage, with the contribution to the sensor signal from the binding pair being an alternating voltage and the contribution to the sensor signal from the non-specifically bound elements being a direct voltage.

11. A sensing apparatus comprising:
    a sensor having a sensing surface and at least one capture molecule attached to the sensing surface for forming a binding pair with an analyte of interest, the binding pair having a flexible spatial orientation;
    an element that applies a first electromagnetic force to the sensing surface to alter the spatial orientation of the binding pair, wherein the magnitude of the applied first electromagnetic force is less than the binding energy of the binding pair;
    wherein the sensing apparatus is configured to perform a sensor measurement with the binding pair in an initial spatial orientation and to perform a sensor measurement with the binding pair in the altered spatial orientation;
    a processor that derives a sensor signal induced by the binding pair from the sensor measurement with the binding pair in the initial spatial orientation and from the sensor measurement with the binding pair in the altered spatial orientation, wherein the processor is configured to derive the sensor signal induced by the binding pair by calculating a difference between the sensor measurement with the binding pair in the initial spatial orientation and the sensor measurement with the binding pair in the altered spatial orientation; and
    a controller for repeatedly, at a predefined frequency, performing a sensor measurement with the binding pair in the initial spatial orientation, applying the first electromagnetic force, performing the sensor measurement with the binding pair in the altered spatial orientation, and deriving the sensor signal.

12. The sensing apparatus of claim 11, wherein the element that applies a first electromagnetic force is configured to alternate between an attractive electromagnetic force and a repulsive electromagnetic force.

13. The sensing apparatus of claim 11, wherein the predefined frequency is in the interval of 15-25 Hz.

14. The sensing apparatus of claim 11, wherein the applied first electromagnetic force does not alter the spatial orientation of contaminants such that a signal contribution from the contaminants is filtered out from the derived sensor signal.

15. The sensing apparatus of claim 14, wherein the sensor signal is a voltage, with the contribution to the sensor signal from the binding pair being an alternating voltage and the contribution to the sensor signal from the contaminants being a direct voltage.

16. The sensing apparatus of claim 11, wherein the applied first electromagnetic force does not alter the spatial orientation of non-specifically bound elements such that a signal contribution from the non-specifically bound elements is filtered out from the derived sensor signal.

17. The sensing apparatus of claim 16, wherein the sensor signal is a voltage, with the contribution to the sensor signal from the binding pair being an alternating voltage and the contribution to the sensor signal from the non-specifically bound elements being a direct voltage.

* * * * *